(12) United States Patent
Yang et al.

(10) Patent No.: US 12,011,718 B2
(45) Date of Patent: Jun. 18, 2024

(54) BLOOD DIAGNOSTIC DEVICE

(71) Applicant: GIST(Gwangju Institute of Science and Technology), Gwangju (KR)

(72) Inventors: Sung Yang, Gwangju (KR); Ji Chul Hyun, Gwangju (KR); Yu Gyung Jung, Gwangju (KR)

(73) Assignee: GIST(Gwangju Institute of Science and Technology), Gwangju (KR)

( * ) Notice: Subject to any disclaimer, the term of this patent is extended or adjusted under 35 U.S.C. 154(b) by 774 days.

(21) Appl. No.: 17/162,753

(22) Filed: Jan. 29, 2021

(65) Prior Publication Data

US 2021/0146363 A1 May 20, 2021

Related U.S. Application Data

(63) Continuation of application No. PCT/KR2019/008538, filed on Jul. 11, 2019.

(30) Foreign Application Priority Data

Jul. 31, 2018 (KR) .................. 10-2018-0089233

(51) Int. Cl.
*B01L 3/00* (2006.01)
*G01N 15/10* (2006.01)
(Continued)

(52) U.S. Cl.
CPC .... *B01L 3/502761* (2013.01); *G01N 15/1023* (2024.01); *G01N 15/1031* (2013.01);
(Continued)

(58) Field of Classification Search
CPC ....... B01L 3/502761; B01L 2200/0652; B01L 2300/0636; B01L 2300/0645;
(Continued)

(56) References Cited

U.S. PATENT DOCUMENTS 9,975,147 B2 * 5/2018 Astier .................. B07B 1/4609
2008/0003142 A1 * 1/2008 Link ................ B01L 3/502784
264/219
(Continued)

FOREIGN PATENT DOCUMENTS

KR 10-2001-0031949 A 4/2001
KR 10-2017-0080165 A 7/2017

OTHER PUBLICATIONS

Hyun, Ji-Chul et al. Improved pillar shape for deterministic lateral displacement separation method to maintain separation efficiency over a long period of time. Separation and Purification Technology, 2017, vol. 172, pp. 258-267. See abstract; pp. 258, 261; and figures 1, 2.

(Continued)

*Primary Examiner* — William H. Beisner
*Assistant Examiner* — Danielle B Henkel
(74) *Attorney, Agent, or Firm* — Studebaker & Brackett PC

(57) ABSTRACT

The present invention relates to a blood diagnostic device, which includes one or more blood input parts into which blood is injected, a deterministic lateral displacement separation part which communicates with the blood input part to form a blood flow path along which the blood flows and separates white blood cells from remaining blood components, a first microchannel which communicates with the deterministic lateral displacement separation part so that the white blood cells separated through the deterministic lateral displacement separation part flow therein, one or more second microchannels which communicate with the deterministic lateral displacement separation part so that the remaining blood components separated through the deterministic lateral displacement separation part flow therein, a first discharge part which communicates with the first microchannel so that the white blood cells flowing in the first (Continued)

microchannel are discharged therethrough, and a second discharge part which communicates with the second microchannel.

7 Claims, 4 Drawing Sheets

(51) Int. Cl.
*G01N 15/1031* (2024.01)
*G01N 33/49* (2006.01)
*G01N 15/01* (2024.01)

(52) U.S. Cl.
CPC .... *G01N 33/491* (2013.01); *B01L 2200/0652* (2013.01); *B01L 2300/0636* (2013.01); *B01L 2300/0645* (2013.01); *B01L 2300/0819* (2013.01); *G01N 2015/016* (2024.01)

(58) Field of Classification Search
CPC ....... B01L 2300/0819; B01L 3/502753; B01L 2400/086; B01L 2300/0861; G01N 15/1031; G01N 15/1056; G01N 33/491; G01N 2015/008; G01N 2015/1006; G01N 2015/1062; G01N 33/49
See application file for complete search history.

(56) References Cited

U.S. PATENT DOCUMENTS

| | | | |
|---|---|---|---|
| 2009/0066315 A1* | 3/2009 | Hu | G01N 15/1056 324/71.4 |
| 2014/0174994 A1 | 6/2014 | Bemate | |
| 2016/0121331 A1* | 5/2016 | Kapur | B01L 3/502746 435/309.1 |

OTHER PUBLICATIONS

Choi, Jongchan et al. On-chip extraction of intracellular molecules in white blood cells from whole blood, Scientific Reports. Oct. 14, 2015, vol. 5, Article 15167, pp. 1-12. See abstract; and figure 1.
Zheng, Yi et al., Lab on a Chip, vol. 13, pp. 2464-2483.(Dec. 31, 2013).
Davis, John A. et al. Deterministic hydrodynamics: Taking blood apart. PNAS. Oct. 3, 2006, vol. 103, No. 40, pp. 14779-14784. See abstract; and figure 2, 3.
GIST. Oct. 21, 2015, pp. 1-9 (Lee, Sukho. [Press Release] Professor Sung Yang's Research Team Developed an Integrated Microfluidic Chip to Separate White Blood Cells from Whole Blood without Using Reagents). Retrieved from [URL: https://www.gist.ac.kr/kr/html/sub07/070102.html?mode=V&no=177621]. See press release, figure explanation.
May 11, 2018, pp. 1-2, (Kwon, Hye Kyung. DLD Separation-Lysis. RadianQbio, Registered 20 Types Products or More at US-FDA. KPENEWS). Retrieved from [URL: http://kpenews.com/View.aspx?No=15454]. See p. 1.
Tran, Trung S. H. et al. Open channel deterministic lateral displacement for particle and cell sorting. Lab on a Chip, 2017, vol. 17, pp. 3592-3600 See abstract; and figures 1, 3.
Office Action issued in KR 10-2018-0089233; mailed by the Korean Intellectual Property Office on Nov. 5, 2019.
International Search Report issued in PCT/KR2019/008538; mailed Oct. 10, 2019.

\* cited by examiner

BLOOD DIAGNOSTIC DEVICE

CROSS-REFERENCE TO RELATED APPLICATION

The present invention is a continuation of International Patent Application No. PCT/KR2019/008538, filed on Jul. 11, 2019, which is based upon and claims the benefit of priority to Korean Application No. 10-2018-0089233 filed on Jul. 31, 2018. The disclosures of the above-listed applications are hereby incorporated by reference herein in their entirety.

BACKGROUND

1. Field of the Invention

The present invention relates to a blood diagnostic device, and more particularly, to a blood diagnostic device capable of differentially diagnosing a bacterial infection by separating blood components.

2. Discussion of Related Art

Upper respiratory infections refer to infections above the lung, including a cold.

Symptoms caused by upper respiratory infections include fever and coughing.

The upper respiratory infections are mainly divided into viral infections and bacterial infections.

Since there is no difference in symptoms between the viral infection and the bacterial infection, the viral and bacterial infections are difficult to diagnose, and treatment methods thereof are also very different.

For example, the viral infection can usually be naturally healed within 7 days to 10 days, but the bacterial infection should be treated by prescribing antibiotics.

Only about 5% to 10% of all patients having upper respiratory infections have bacterial infections requiring a prescription for antibiotics.

In patients infected with bacteria, the number of white blood cells is increased as compared with a normal person.

For example, according to clinical data, the total number of white blood cells in patients with a bacterial infection is about 1.5 to 2 times that in a normal person. In addition, in the case of a bacterial infection, it is known that the total number of white blood cells is 1.5 times than that of a viral infection.

In addition, in the case of patients infected with bacteria, it is known that a level of a cyclic C-reactive protein in a cyclic form present in plasma is 1.5 to 2 times higher than that in normal person. In addition, in the case of a bacterial infection, it is known that a level of a C-reactive protein is 5 to 8 times higher than that of a viral infection.

Meanwhile, such antibiotics should be prescribed only for bacterial infections, but since it is difficult for local small hospitals to have large-scale test instruments such as cell counters or chemical analyzers capable of differentiating viral infections and bacterial infections and to have manpower according to the large-scale test instruments, antibiotics are prescribed even for viral infections, which causes abuse of antibiotics and also causes resistance to antibiotics in patients.

SUMMARY OF THE INVENTION

The present invention is directed to providing a blood diagnostic device in which even a non-specialist may easily use the blood diagnostic device to separate blood components without a need for a large-scale test instrument, a viral infection and a bacterial infection may be easily differentially diagnosed through blood separation, and antibiotics may be appropriately prescribed to prevent the abuse of antibiotics.

According to an aspect of the present invention, there is provided a blood diagnostic device including one or more blood input parts into which blood is injected, a deterministic lateral displacement separation part which communicates with the blood input part to form a blood flow path along which the blood flows and separates white blood cells from remaining blood components, a first microchannel which communicates with the deterministic lateral displacement separation part so that the white blood cells separated through the deterministic lateral displacement separation part flow therein, one or more second microchannels which communicate with the deterministic lateral displacement separation part so that the remaining blood components separated through the deterministic lateral displacement separation part flow therein, a first discharge part which communicates with the first microchannel so that the white blood cells flowing in the first microchannel are discharged therethrough, and a second discharge part which communicates with the second microchannel so that the remaining blood components flowing in the second microchannel are discharged therethrough.

The deterministic lateral displacement separation part may include a plurality of fillers disposed at intervals in a matrix direction in the blood flow path.

The filler may include a vertical portion disposed in a length direction of the blood flow path, a lateral portion disposed in a lateral direction with respect to the vertical portion from one side of the vertical portion, a first inclined portion disposed to be inclined at an obtuse angle with respect to the lateral portion from the lateral portion, and a second inclined portion disposed to be inclined at an acute angle with respect to the vertical portion from the other side of the vertical portion and connected to the first inclined portion.

The plurality of fillers may be disposed such that the first inclined portion and the second inclined portion face in the same direction.

The blood diagnostic device may further include a third microchannel which branches off from the second microchannel so that, among the remaining blood components flowing in the second microchannel, plasma flows therein, and a third discharge part which communicates with the third microchannel so that the plasma flowing in the third microchannel is discharged therethrough.

The second microchannel may include a reduction channel portion which communicates with the deterministic lateral displacement separation part and has a micro-flow path along which the remaining blood components flow and an expansion channel portion which communicates with the reduction channel portion and has an expansion flow path having a width greater than that of the micro-flow path of the reduction channel portion, and the third microchannel may have a plasma micro-flow path, of which a width is smaller than that of the expansion flow path of the expansion channel portion, formed therein, and may branch in the same direction as the reduction channel portion at a position spaced apart from a neck portion formed between the reduction channel portion and the expansion channel portion.

The blood diagnostic device may further include a white blood cell counting unit disposed at the first microchannel to count the number of the white blood cells flowing in the first microchannel.

The white blood cell counting unit may include a first electrode disposed in the first microchannel, one pair of second electrodes disposed opposite to each other in the first microchannel with the first electrode interposed therebetween, a power supply configured to apply power to the first electrode so that a current is applied to the one pair of second electrodes, and a current measurement part configured to measure the current flowing in the one pair of second electrodes.

The first electrode and the one pair of second electrodes may be disposed at intervals in a lateral direction with respect to a length direction of the first microchannel.

ADVANTAGEOUS EFFECTS

According to the present invention, even non-specialist can easily use a blood diagnostic device to separate blood components without need for a large-scale test instrument. In addition, a viral infection and a bacterial infection can be easily differentially diagnosed through blood separation, and antibiotics can be appropriately prescribed to prevent the abuse of antibiotics

DETAILED DESCRIPTION OF EXEMPLARY EMBODIMENTS

Figure 1:
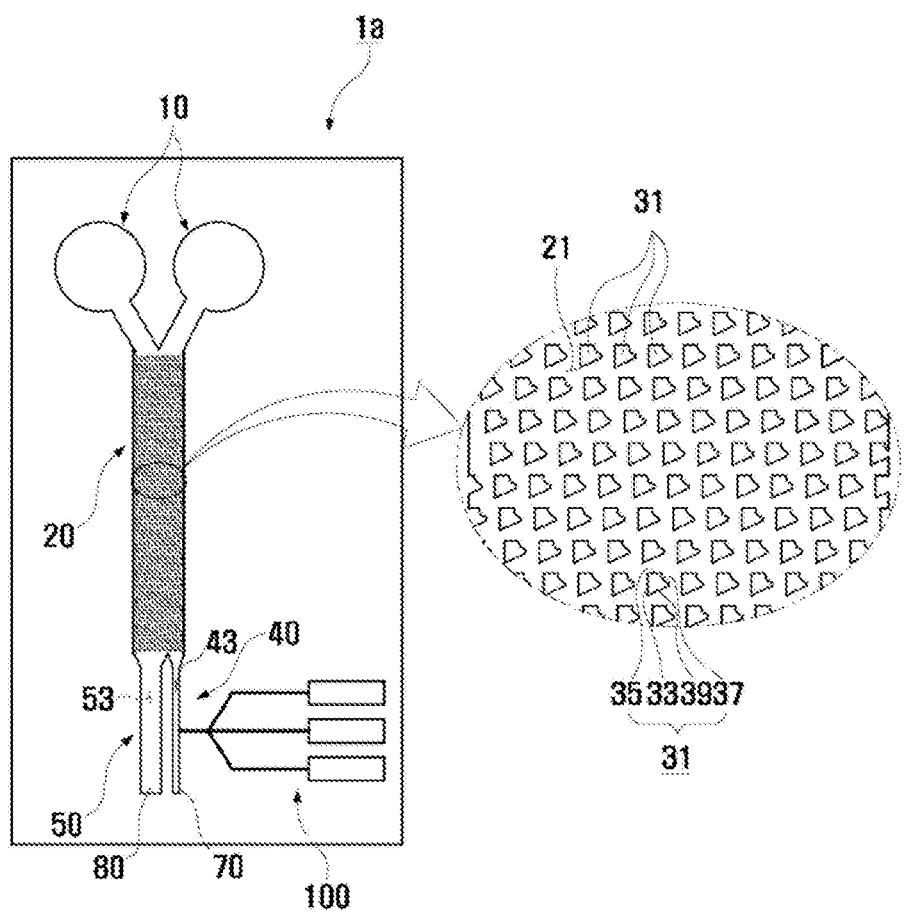
FIG. 1 is a view of a configuration of a blood diagnostic device according to one embodiment of the present invention.

The advantages and features of the present invention and methods for accomplishing the same will be more clearly understood from embodiments to be described in detail below with reference to the accompanying drawings. However, the present invention is not limited to the following embodiments but may be implemented in various different forms. Rather, these embodiments are provided only to complete the disclosure of the present invention and to allow a person with ordinary skill in the art, to which the present invention belongs, to understand the category of the present invention.

The terms used in the present specification are for explaining the embodiments rather than limiting the present invention. As used herein, singular expressions, unless defined otherwise in context, include plural expressions. The meaning of "comprises" and/or "comprising" used in this specification does not exclude the existence or addition of one or more other components in addition to the mentioned components. The same reference numerals denote the same components throughout the specification. As used herein, the term "and/or" includes any and all combinations of one or more of the associated components. It will be understood that, although the terms "first," "second," and the like may be used herein to describe various components, these components should not be limited by these terms. These terms are only used to distinguish one element or component from another element or component. Therefore, a first component described below could be termed a second component without departing from the scope and spirit of the present invention.

Unless otherwise defined, all terms (including technical and scientific terms) used in the present specification may be used with the same meaning which may be commonly understood by the person with ordinary skill in the art to which the present invention belongs. It will be further understood that terms defined in commonly used dictionaries should not be interpreted in an idealized or excessive sense unless expressly and specifically defined.

Hereinafter, the present invention will be described in detail with reference to the accompanying drawings.

Prior to the description, it should be noted that components having the same configurations in various embodiments are denoted by identical reference numerals and representatively described in one embodiment and only components different from those in one embodiment are described in the other embodiments.

FIG. 1 illustrates a blood diagnostic device according to one embodiment of the present invention.

As shown in FIG. 1, a blood diagnostic device 1a according to one embodiment of the present invention includes one pair of blood input parts 10, a deterministic lateral displacement separation part 20, a first microchannel 40, a second microchannel 50, a first discharge part 70, and a second discharge part 80.

The blood diagnostic device 1a has an overall rectangular plate shape.

One pair of blood input parts 10 are provided at one side of the blood diagnostic device 1a, and blood, of which blood components are to be separated, is injected into the blood input part 10.

Whole blood is injected into at least one of one pair of blood input parts 10. A physiological saline solution (phosphate-buffered saline) may be injected into the remaining blood input part 10 into which the whole blood is not injected.

In the present embodiment, although one pair of blood input parts 10 are illustrated as being provided, the present invention is not limited thereto, and one or three more blood input parts 10 may be provided.

The deterministic lateral displacement separation part 20 communicates with one pair of blood input parts 10. A blood flow path 21, along which blood input from one pair of blood input parts 10 flows, is formed in the deterministic lateral displacement separation part 20. The deterministic lateral displacement separation part 20 has a rectangular cross-sectional shape having a predetermined length and width.

The blood flow path 21 is provided with a plurality of fillers 31 for separating white blood cells of blood flowing along the blood flow path 21 from the remaining blood components of the blood.

The filler 31 has a polygonal cross-sectional shape of which one side is inclined.

Specifically, the filler 31 has a vertical portion 33 disposed in a length direction of the blood flow path 21, a lateral portion 35 disposed in a lateral direction with respect to the vertical portion 33 from one side of the vertical portion 33, a first inclined portion 37 disposed to be inclined at an obtuse angle with respect to the lateral portion 35 from the lateral portion 35, and a second inclined portion 39 disposed to be inclined at an acute angle with respect to the vertical portion 33 from the other side of the vertical portion 33 and connected to the first inclined portion 37.

The vertical portion 33, the lateral portion 35, and the second inclined portion 39 of each filler 31 have a linear shape, and the first inclined portion 37 has a predetermined radius of curvature and a curved arc shape. Here, in the present embodiment, although the first inclined portion 37 of each filler 31 is illustrated as having the arc shape, the present invention is not limited thereto, and the first inclined portion 37 may have a linear shape.

The plurality of fillers 31 are disposed at intervals in a matrix direction of the blood flow path 21. In addition, the plurality of fillers 31 are disposed such that the lateral portion 35 faces the blood input part 10 and concurrently the first inclined portion 37 and the second inclined portion 39 face in the same direction.

As described above, since the plurality of fillers 31 are disposed in the deterministic lateral displacement separation part 20 to allow blood to flow, white blood cells move in a displacement mode according to an inclined angle of the first inclined portion 37, and the remaining blood components including red blood cells linearly move in a zigzag mode.

That is, as blood passes through each of the fillers 31, white blood cells of the blood move in the displacement mode, and the remaining blood components including red blood cells move in the zigzag mode so that the white blood cells and the remaining blood components are naturally separated from each other.

The first microchannel 40 is disposed opposite to the blood input part 10 with the deterministic lateral displacement separation part 20 interposed therebetween. The first microchannel 40 is provided to communicate with the deterministic lateral displacement separation part 20, and a first micro-flow path 43, along which white blood cells flow, is formed therein. A width of the first micro-flow path 43 is smaller than a width of the blood flow path 21 of the deterministic lateral displacement separation part 20.

In addition, in order to facilitate collection of white blood cells that are separated by moving along the first inclined portion 37 of each filler 31 of the deterministic lateral displacement separation part 20, the first microchannel 40 is disposed toward an orientation position of each of the inclined portions 37 and 39 of each filler 31, for example, at a lower right end portion of the deterministic lateral displacement separation part 20 as shown in FIG. 1.

The second microchannel 50 is disposed opposite to the blood input part 10 with the deterministic lateral displacement separation part 20 interposed therebetween. The second microchannel 50 is provided to communicate with the deterministic lateral displacement separation part 20, and a second micro-flow path 53, along which the remaining blood components excluding white blood cells flow, is formed therein. A width of the second micro-flow path 53 is smaller than the width of the blood flow path 21 of the deterministic lateral displacement separation part 20.

In addition, in order to facilitate collection of the remaining blood components including red blood cells that are separated by moving along the lateral portion 35 of each filler 31 of the deterministic lateral displacement separation part 20, the second microchannel 50 is disposed at a lower left end portion of the deterministic lateral displacement separation part 20 as shown in FIG. 1.

Here, in the present embodiment, although only one second microchannel 50 is illustrated as being provided, the present invention is not limited thereto, and a plurality of second microchannels 50 may be provided.

The first discharge part 70 communicates with the first microchannel 40 so that white blood cells flowing along the first microchannel 40 are discharged therethrough.

The second discharge part 80 communicates with the second microchannel 50 so that the remaining blood components including red blood cells flowing along the second microchannel 50 are discharged therethrough.

In addition, the blood diagnostic device 1a according to one embodiment of the present invention may further include a white blood cell counting unit 100.

The white blood cell counting unit 100 is disposed at the first microchannel 40 and counts the number of white blood cells flowing along the first microchannel 40.

Figure 2A:
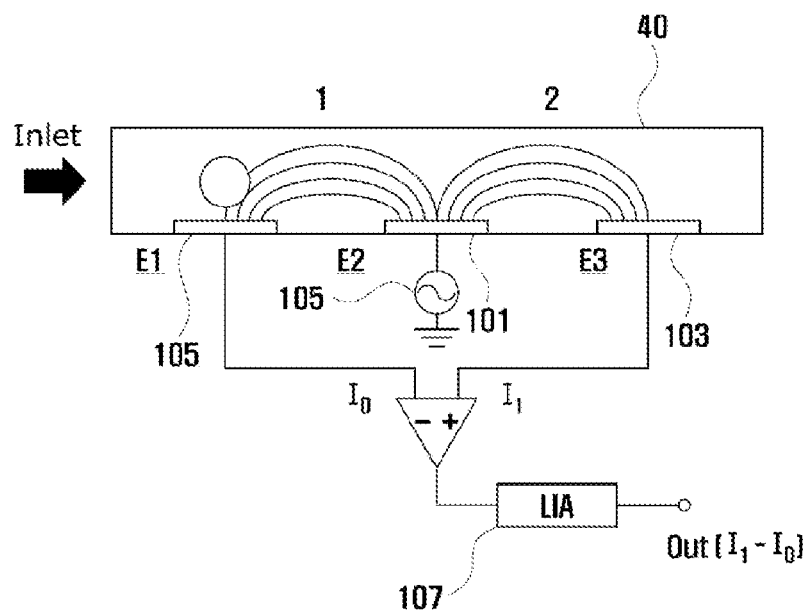
FIGS. 2A and 2B are a view and a graph illustrating and showing a configuration and a counting process of a white blood cell counting unit of FIG. 1.
Figure 2B:
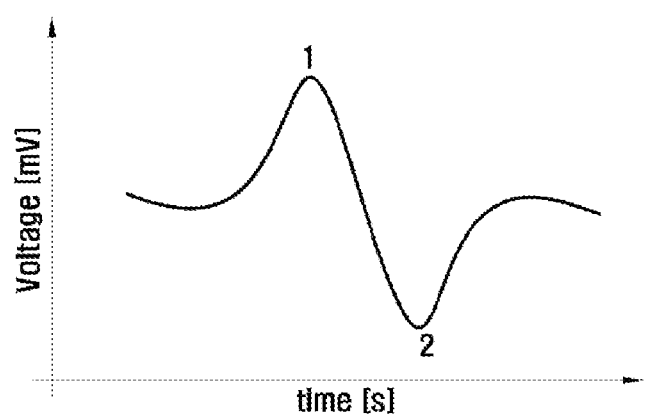

As shown in FIG. 2A, the white blood cell counting unit 100 includes a first electrode 101 made of an electrically conductive conductor, one pair of second electrodes 103 made of an electrically conductive conductor, a power supply 105, and a current measurement part 107.

The first electrode 101 and one pair of second electrodes 103 are disposed at intervals in a lateral direction with respect to a length direction of the first microchannel 40.

That is, one pair of second electrodes 103 are disposed opposite to each other with the first electrode 101 interposed therebetween. A distance between the first electrode 101 and each second electrode 103 has a size allowing a current to be applied to the second electrode 103 when power is applied to the first electrode 101.

The power supply 105 applies power to the first electrode 101 so that a current is applied to one pair of second electrodes 103.

The current measurement part 107 measures a current flowing in one pair of second electrodes 103.

Accordingly, a voltage is applied to the first electrode 101 and a current of each second electrode 103 is measured. When general noise is removed from the measured current, and as shown in FIG. 2A, when white blood cells pass through regions "1" and "2", as shown in 2B, peaks occur above and below due to a cut-off of the measured current. Accordingly, one peak may be calculated as one white blood cell passing through the first microchannel 40.

By using such a principle, the number of white blood cells passing through the first microchannel 40 can be simply and accurately counted.

Here, in the present embodiment, although the white blood cell counting unit 100 is illustrated as being provided, the white blood cell counting unit 100 may be optionally provided as necessary.

Due to such a configuration, in the blood diagnostic device 1a according to one embodiment of the present invention, when blood is injected into the blood input part 10, the blood is separated into white blood cells and the remaining blood components while passing through the deterministic lateral displacement separation part 20 in which the plurality of fillers 31 are disposed, and thus, the white blood cells are discharged to the first discharge part 70 through the first microchannel 40, and the remaining blood components including red blood cells are discharged to the second discharge part 80 through the second microchannel 50. Accordingly, infected blood can be easily separated into white blood cells and the remaining components including red blood cells.

In this case, by grasping the number of white blood cells counted by the white blood cell counting unit 100 provided at the first microchannel 40, it is possible to differentially diagnose a bacterial infection in blood. In addition, a separate test device is used to grasp a level of a C-reactive protein contained in the remaining blood components discharged to the second discharge part 80, thereby differentially diagnosing a bacterial infection in blood.

Meanwhile, when the white blood cell counting unit 100 is not provided in the blood diagnostic device 1a, a separate test device may be used to grasp the number of white blood cells discharged to the first discharge part 70, thereby differentially diagnosing a bacterial infection in blood.

Accordingly, only when the number of white blood cells or a level of a C-reactive protein deviates from a reference range and thus it is determined that blood is infected with bacterial, can antibiotics be prescribed, thereby preventing the abuse of antibiotics by patients.

Figure 3:
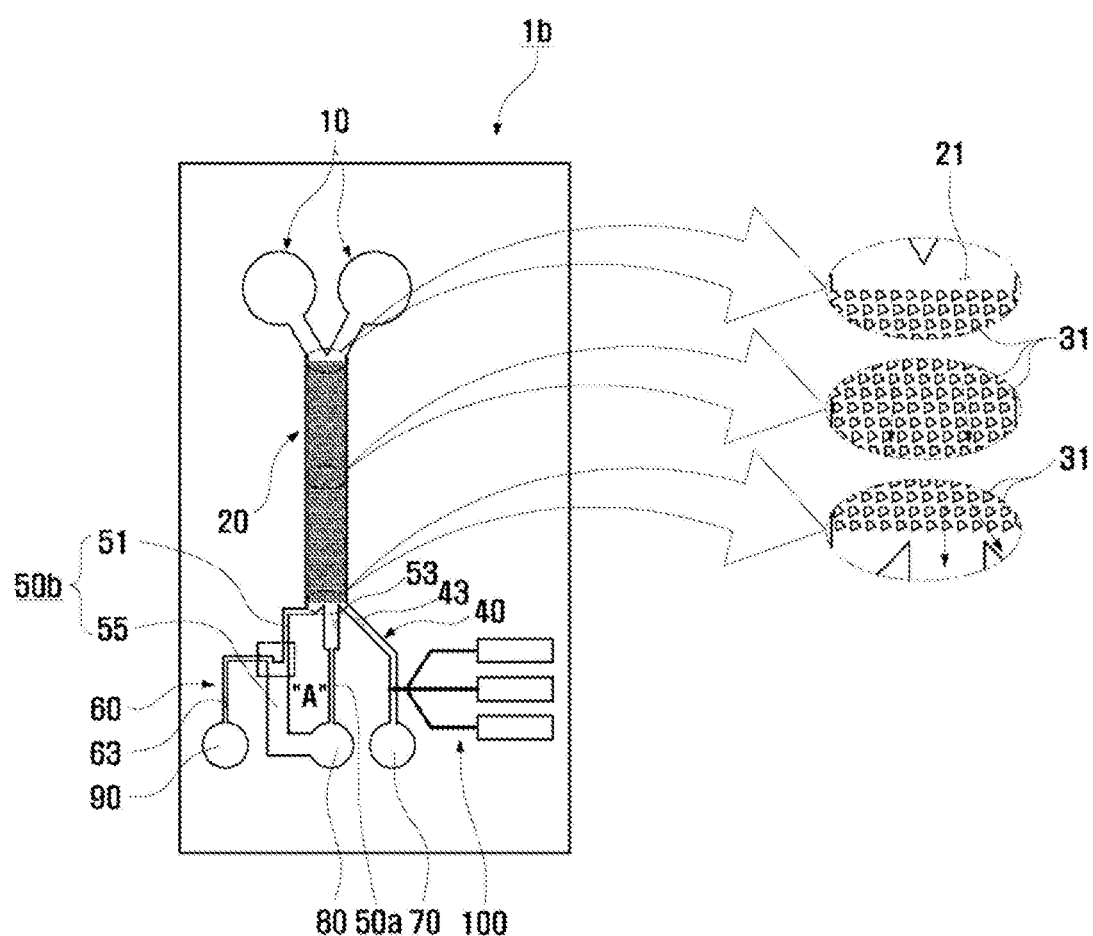
FIG. 3 is a view of a configuration of a blood diagnostic device according to another embodiment of the present invention.
Figure 4:
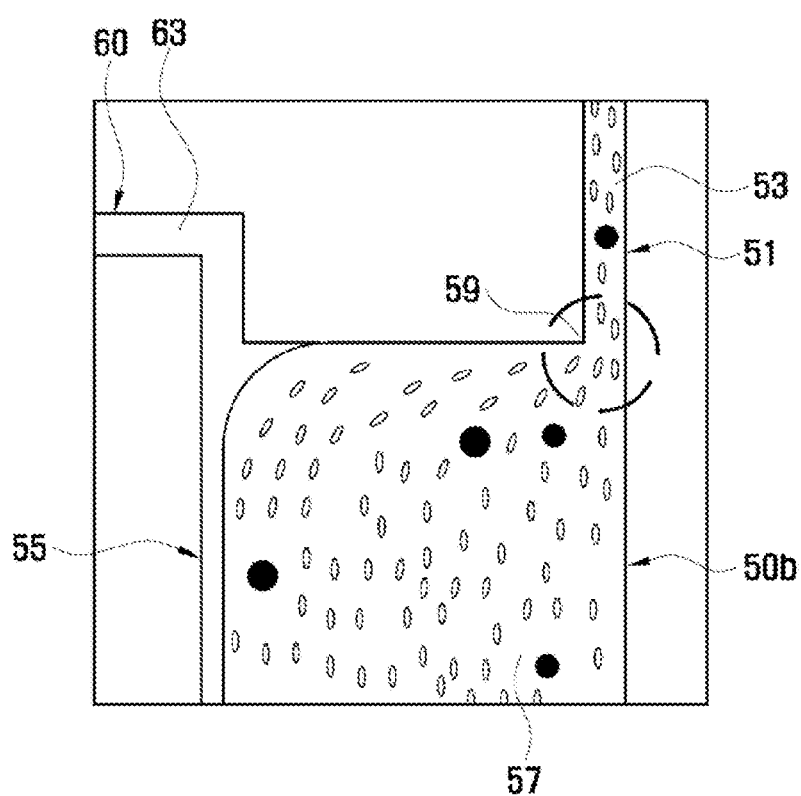
FIG. 4 is a schematic view illustrating a blood flow in portion "A" of a second microchannel of FIG. 3.

FIGS. 3 and 4 are views illustrating a configuration of a blood diagnostic device according to another embodiment of the present invention.

As shown in the drawings, unlike the above-described embodiment, in a blood diagnostic device 1b according to another embodiment of the present invention, one pair of second microchannels 50a and 50b are formed to branch off from a lower end portion of a deterministic lateral displacement separation part 20.

In addition, a third microchannel 60 branches off from one second microchannel 50b of one pair of second microchannels 50a and 50b.

Plasma of the remaining blood components flowing along the second microchannel 50b flows along the third microchannel 60.

The third microchannel 60 communicates with a third discharge part 90, and plasma flowing along the third microchannel 60 is discharged through the third discharge part 90.

Meanwhile, the second microchannel 50b, off from which the third microchannel 60 branches, includes a reduction channel portion 51 and an expansion channel portion 55.

The reduction channel portion 51 is provided to communicate with the deterministic lateral displacement separation part 20, and a second micro-flow path 53, along which the remaining blood components including red blood cells flow, is formed therein. A width of the second micro-flow path 53 is smaller than a width of a blood flow path 21 of the deterministic lateral displacement separation part 20.

The expansion channel portion 55 is provided to communicate with the reduction channel portion 51, and an expansion flow path 57, of which a width is greater than the width of the second micro-flow path 53, is formed therein.

Accordingly, a neck portion 59 is formed in a boundary region between the reduction channel portion 51 and the expansion channel portion 55 of the second microchannel 50b.

Meanwhile, the third microchannel 60 branches in the same direction as the reduction channel portion 51 at a position spaced apart from the neck portion 59 formed between the reduction channel portion 51 and the expansion channel portion 55, for example, branches off from a region opposite to a direction in which the remaining blood components excluding white blood cells are sprayed from the reduction channel portion 51 to the expansion channel portion 55. In addition, the third microchannel 60 forms a plasma micro-flow path 63 of which a width is smaller than that of the expansion flow path 57 of the expansion channel portion 55 of the second microchannel 50b.

Since the third microchannel 60 is disposed to communicate with the second microchannel 50b, as shown in FIG. 4, a left region of the expansion channel portion 55, for example, a cell free layer of the third microchannel 60, is formed by an inertial force generated in the neck portion 59. Accordingly, only plasma of the remaining blood components is discharged through the third microchannel 60, and the remaining blood components excluding white blood cells and plasma are discharged to the second discharge part 80 through the expansion channel portion 55.

As described above, in the blood diagnostic device 1b according to another embodiment of the present invention, the expansion channel portion 55 is provided in one region of the second microchannel 50b along which the remaining blood components excluding white blood cells flow, and the third microchannel 60 branches off from the region opposite to the direction in which the remaining blood components excluding white blood cells are sprayed from the reduction channel portion 51 to the expansion channel portion 55. Accordingly, only plasma can be separated through the third microchannel 60.

Due to such a configuration, in the blood diagnostic device 1b according to another embodiment of the present invention, when blood is injected into a blood input part 10, the blood is separated into white blood cells and the remaining blood components while passing through the deterministic lateral displacement separation part 20 in which a plurality of fillers 31 are disposed, and thus, the white blood cells are discharged to a first discharge part 70 through a first microchannel 40, and the remaining blood components including red blood cells are discharged to a second discharge part 80 through the second microchannels 50a and 50b.

Meanwhile, the expansion channel portion 55 is provided in one region of the second microchannel 50b along which the remaining blood components excluding while blood cells flow, and the third microchannel 60 branches off therefrom at the same time, thereby separating only plasma through the third microchannel through 60 to discharge the separated plasma to the third discharge part 90.

In this case, by grasping the number of white blood cells counted by a white blood cell counting unit 100 provided at the first microchannel 40, it is possible to differentially diagnose a bacterial infection in blood. In addition, a separate test device is used to grasp a level of a C-reactive protein contained in the plasma discharged to the third discharge part 90, thereby differentially diagnosing a bacterial infection in blood.

Meanwhile, when the white blood cell counting unit 100 is not provided in the blood diagnostic device 1b, a separate test device may be used to grasp the number of white blood cells discharged to the first discharge part 70, thereby differentially diagnosing a bacterial infection in blood Accordingly, only when the number of white blood cells or a level of a C-reactive protein deviates from a reference range and thus it is determined that blood is infected with bacterial, are antibiotics prescribed.

As described above, according to the present invention, even a non-specialist can easily use a plate-shaped blood diagnostic device to inject blood components thereto and separate the blood components without need for a large-scale test instrument. In addition, a viral infection and a bacterial infection can be easily differentially diagnosed through blood separation, and antibiotics can be appropriately prescribed to prevent the abuse of antibiotics.

What is claimed is:
1. A blood diagnostic device comprising:
one or more blood input parts into which blood is injected;
a deterministic lateral displacement separation part which
    communicates with the blood input part to form a blood flow path along which the blood flows and separates white blood cells from remaining blood components;

a first microchannel which communicates with the deterministic lateral displacement separation part so that the white blood cells separated through the deterministic lateral displacement separation part flow therein,
wherein the first microchannel comprises a first micro-flow path that is directly connected to a distal end portion of the deterministic lateral displacement separation part;
a first discharge part which communicates with the first microchannel so that the white blood cells flowing in the first microchannel are discharged therethrough;
a first-second microchannel which communicates with the deterministic lateral displacement separation part so that the remaining blood components separated through the deterministic lateral displacement separation part flow therein,
wherein the first-second microchannel comprises a second micro-flow path that is directly connected to the distal end portion of the deterministic lateral displacement separation part;
a second discharge part which communicates with the first-second microchannel so that the remaining blood components flowing in the first-second microchannel are discharged therethrough;
a second-second microchannel which communicates with the deterministic lateral displacement separation part so that the remaining blood components separated through the deterministic lateral displacement separation part flow therein,
wherein the second-second microchannel comprises:
    a reduction channel portion which communicates with the deterministic lateral displacement separation part and has a micro-flow path along which the remaining blood components flow, wherein the reduction channel portion has a first end that is directly connected to the distal end portion of the deterministic lateral displacement separation part; and
    a expansion channel portion which communicates with the reduction channel portion, wherein the expansion channel portion has a first end that is directly connected to a second end of the reduction channel portion, and has a second end that is directly connected to the second discharge part,
wherein the second discharge part communicates with both the first-second microchannel and the expansion channel portion, so that the remaining blood components flowing in the first-second microchannel and the expansion channel portion are discharged therethrough;
a third microchannel which branches off from the second-second microchannel so that, among the remaining blood components flowing in the second microchannel, plasma flows therein; and
a third discharge part which communicates with the third microchannel so that the plasma flowing in the third microchannel is discharged therethrough,
wherein the third microchannel comprises a plasma micro-flow path having a first end that is directly connected to the second end of the reduction channel portion, and having a second end that is directly connected to the third discharge part,
wherein the plasma micro-flow path is extended in the same direction as the reduction channel portion at a position spaced apart from a neck portion formed between the reduction channel portion and the expansion channel portion, and
wherein a width of the second micro-flow path is smaller than a width of a blood flow path of the deterministic lateral displacement separation part, a width of the expansion channel portion is greater than the width of the second micro-flow path, the width of the expansion channel portion is greater than a width of the reduction channel portion, and a width of the plasma micro-flow path is smaller than the width of the expansion channel portion.

2. The blood diagnostic device of claim 1, wherein the deterministic lateral displacement separation part includes a plurality of fillers disposed at intervals in a matrix direction in the blood flow path.

3. The blood diagnostic device of claim 2, wherein the filler includes:
    a vertical portion disposed in a length direction of the blood flow path;
    a lateral portion disposed in a lateral direction with respect to the vertical portion from one side of the vertical portion;
    a first inclined portion disposed to be inclined at an obtuse angle with respect to the lateral portion from the lateral portion; and
    a second inclined portion disposed to be inclined at an acute angle with respect to the vertical portion from the other side of the vertical portion and connected to the first inclined portion.

4. The blood diagnostic device of claim 3, wherein the plurality of fillers are disposed such that the first inclined portion and the second inclined portion face in the same direction.

5. The blood diagnostic device of claim 1, further comprising a white blood cell counting unit disposed at the first microchannel to count the number of the white blood cells flowing in the first microchannel.

6. The blood diagnostic device of claim 5, wherein the white blood cell counting unit includes:
    a first electrode disposed in the first microchannel;
    one pair of second electrodes disposed opposite to each other in the first microchannel with the first electrode interposed therebetween;
    a power supply configured to apply power to the first electrode so that a current is applied to the one pair of second electrodes; and
    a current measurement part configured to measure the current flowing in the one pair of second electrodes.

7. The blood diagnostic device of claim 6, wherein the first electrode and the one pair of second electrodes are disposed at intervals in a lateral direction with respect to a length direction of the first microchannel.

* * * * *